(12) United States Patent
Hodgkinson

(10) Patent No.: US 9,237,892 B2
(45) Date of Patent: Jan. 19, 2016

(54) BUTTRESS ATTACHMENT TO THE CARTRIDGE SURFACE

(71) Applicant: Covidien LP, Mansfield, MA (US)

(72) Inventor: Gerald N. Hodgkinson, Guilford, CT (US)

(73) Assignee: Covidien LP, Mansfield, MA (US)

( * ) Notice: Subject to any disclaimer, the term of this patent is extended or adjusted under 35 U.S.C. 154(b) by 413 days.

(21) Appl. No.: 13/719,630

(22) Filed: Dec. 19, 2012

(65) Prior Publication Data

US 2013/0153635 A1 Jun. 20, 2013

Related U.S. Application Data

(63) Continuation-in-part of application No. 13/586,261, filed on Aug. 15, 2012, which is a continuation-in-part of application No. 13/325,481, filed on Dec. 14, 2011.

(51) Int. Cl.
*A61B 17/04* (2006.01)
*A61B 17/072* (2006.01)
*A61B 17/115* (2006.01)
*A61B 17/00* (2006.01)

(52) U.S. Cl.
CPC ....... *A61B 17/07207* (2013.01); *A61B 17/0401* (2013.01); *A61B 17/07292* (2013.01); *A61B 17/1155* (2013.01); *A61B 2017/00477* (2013.01); *A61B 2017/0406* (2013.01)

(58) Field of Classification Search
CPC .................. A61B 17/072; A61B 2017/07214; A61B 17/115; A61B 2017/00526; A61B 17/064; A61B 17/068; A61B 17/0682; A61B 17/1114; A61B 2017/00004; A61B 2017/00818; A61B 17/0401; A61B 2017/0406; A61B 17/07292
USPC ............. 227/179, 175.1, 176.1, 180.1, 181.1; 606/215, 151, 139
See application file for complete search history.

(56) References Cited

U.S. PATENT DOCUMENTS

| 3,054,406 A | 9/1962 | Usher |
| 3,079,606 A | 3/1963 | Bobrov et al. |
| 3,124,136 A | 3/1964 | Usher |

(Continued)

FOREIGN PATENT DOCUMENTS

| CA | 2 667 434 | 5/2008 |
| CN | 101310680 A | 11/2008 |

(Continued)

OTHER PUBLICATIONS

Extended European Search Report corresponding to EP 08 72 6500.5, completed Feb. 20, 2014 and mailed Mar. 3, 2014; (7 pp).

(Continued)

*Primary Examiner* — Andrew M Tecco
*Assistant Examiner* — Chelsea Stinson

(57) ABSTRACT

An end effector for use with a surgical apparatus. The end effector comprising a staple cartridge having a tissue contacting surface defining a central longitudinal slot and an anvil plate having a tissue contacting surface defining a central longitudinal slot. A surgical buttress releasbly disposed on the tissue contacting surfaces of each of the staple cartridge and anvil plate. An adhesive tape is disposed over the central longitudinal slot of each of the staple cartridge and anvil plate and configured retain the respective surgical buttress atop the respective tissue contacting surface.

15 Claims, 8 Drawing Sheets

(56) References Cited

U.S. PATENT DOCUMENTS

| | | | |
|---|---|---|---|
| 3,490,675 A | 1/1970 | Green et al. | |
| 3,499,591 A | 3/1970 | Green | |
| 4,347,847 A | 9/1982 | Usher | |
| 4,354,628 A | 10/1982 | Green | |
| 4,429,695 A | 2/1984 | Green | |
| 4,452,245 A | 6/1984 | Usher | |
| 4,605,730 A | 8/1986 | Shalaby et al. | |
| 4,655,221 A | 4/1987 | Devereux | |
| 4,834,090 A | 5/1989 | Moore | |
| 4,838,884 A | 6/1989 | Dumican et al. | |
| 4,927,640 A | 5/1990 | Dahlinder et al. | |
| 4,930,674 A | 6/1990 | Barak | |
| 5,002,551 A | 3/1991 | Linsky et al. | |
| 5,014,899 A | 5/1991 | Presty et al. | |
| 5,040,715 A | 8/1991 | Green et al. | |
| 5,065,929 A | 11/1991 | Schulze et al. | |
| 5,205,459 A | 4/1993 | Brinkerhoff et al. | |
| 5,263,629 A * | 11/1993 | Trumbull et al. | 227/181.1 |
| 5,307,976 A | 5/1994 | Olson et al. | |
| 5,312,023 A | 5/1994 | Green et al. | |
| 5,314,471 A | 5/1994 | Brauker et al. | |
| 5,318,221 A | 6/1994 | Green et al. | |
| 5,326,013 A | 7/1994 | Green et al. | |
| 5,332,142 A | 7/1994 | Robinson et al. | |
| 5,344,454 A | 9/1994 | Clarke et al. | |
| 5,392,979 A | 2/1995 | Green et al. | |
| 5,397,324 A | 3/1995 | Carroll et al. | |
| 5,425,745 A | 6/1995 | Green et al. | |
| 5,441,193 A | 8/1995 | Gravener | |
| 5,441,507 A | 8/1995 | Wilk et al. | |
| 5,443,198 A | 8/1995 | Viola et al. | |
| 5,468,253 A | 11/1995 | Bezwada et al. | |
| 5,503,638 A | 4/1996 | Cooper et al. | |
| 5,542,594 A | 8/1996 | McKean et al. | |
| 5,549,628 A | 8/1996 | Cooper et al. | |
| 5,575,803 A | 11/1996 | Cooper et al. | |
| 5,653,756 A | 8/1997 | Clarke et al. | |
| 5,683,809 A | 11/1997 | Freeman et al. | |
| 5,690,675 A | 11/1997 | Sawyer et al. | |
| 5,702,409 A | 12/1997 | Rayburn et al. | |
| 5,752,965 A | 5/1998 | Francis et al. | |
| 5,762,256 A | 6/1998 | Mastri et al. | |
| 5,766,188 A | 6/1998 | Igaki | |
| 5,769,892 A | 6/1998 | Kingwell | |
| 5,782,396 A | 7/1998 | Mastri et al. | |
| 5,799,857 A | 9/1998 | Robertson et al. | |
| 5,810,855 A | 9/1998 | Rayburn et al. | |
| 5,814,057 A | 9/1998 | Oi et al. | |
| 5,833,695 A | 11/1998 | Yoon | |
| 5,843,096 A | 12/1998 | Igaki et al. | |
| 5,895,412 A | 4/1999 | Tucker | |
| 5,895,415 A | 4/1999 | Chow et al. | |
| 5,902,312 A | 5/1999 | Frater et al. | |
| 5,908,427 A | 6/1999 | McKean et al. | |
| 5,915,616 A | 6/1999 | Viola et al. | |
| 5,931,847 A | 8/1999 | Bittner et al. | |
| 5,964,394 A | 10/1999 | Robertson | |
| 5,964,774 A | 10/1999 | McKean et al. | |
| 5,997,895 A | 12/1999 | Narotam et al. | |
| 6,019,791 A | 2/2000 | Wood | |
| 6,030,392 A | 2/2000 | Dakov et al. | |
| 6,032,849 A | 3/2000 | Mastri et al. | |
| 6,045,560 A | 4/2000 | McKean et al. | |
| 6,063,097 A | 5/2000 | Oi et al. | |
| 6,080,169 A | 6/2000 | Turtel | |
| 6,099,551 A | 8/2000 | Gabbay | |
| 6,149,667 A | 11/2000 | Hovland et al. | |
| 6,155,265 A | 12/2000 | Hammerslag | |
| 6,210,439 B1 | 4/2001 | Firmin et al. | |
| 6,214,020 B1 | 4/2001 | Mulhauser et al. | |
| 6,241,139 B1 | 6/2001 | Milliman et al. | |
| 6,258,107 B1 | 7/2001 | Balazs et al. | |
| 6,267,772 B1 | 7/2001 | Mulhauser et al. | |
| 6,273,897 B1 | 8/2001 | Dalessandro et al. | |
| 6,280,453 B1 | 8/2001 | Kugel et al. | |
| 6,299,631 B1 | 10/2001 | Shalaby | |
| 6,312,457 B1 | 11/2001 | DiMatteo et al. | |
| 6,312,474 B1 | 11/2001 | Francis et al. | |
| 6,325,810 B1 * | 12/2001 | Hamilton | A61B 17/07207 227/175.1 |
| 6,330,965 B1 | 12/2001 | Milliman et al. | |
| 6,436,030 B2 | 8/2002 | Rehil | |
| 6,454,780 B1 | 9/2002 | Wallace | |
| 6,461,368 B2 | 10/2002 | Fogarty et al. | |
| 6,503,257 B2 | 1/2003 | Grant et al. | |
| 6,514,283 B2 | 2/2003 | DiMatteo et al. | |
| 6,517,566 B1 | 2/2003 | Hovland et al. | |
| 6,551,356 B2 | 4/2003 | Rousseau | |
| 6,592,597 B2 | 7/2003 | Grant et al. | |
| 6,638,285 B2 | 10/2003 | Gabbay | |
| 6,652,594 B2 | 11/2003 | Francis et al. | |
| 6,656,193 B2 * | 12/2003 | Grant | A61B 17/072 227/175.1 |
| 6,669,735 B1 | 12/2003 | Pelissier | |
| 6,677,258 B2 | 1/2004 | Carroll et al. | |
| 6,685,714 B2 | 2/2004 | Rousseau | |
| 6,702,828 B2 | 3/2004 | Whayne | |
| 6,704,210 B1 | 3/2004 | Myers | |
| 6,723,114 B2 | 4/2004 | Shalaby | |
| 6,726,706 B2 | 4/2004 | Dominguez | |
| 6,736,823 B2 | 5/2004 | Darois et al. | |
| 6,736,854 B2 | 5/2004 | Vadurro et al. | |
| 6,746,458 B1 | 6/2004 | Cloud | |
| 6,773,458 B1 | 8/2004 | Brauker et al. | |
| 6,896,684 B2 | 5/2005 | Monassevitch et al. | |
| 6,927,315 B1 | 8/2005 | Heinecke et al. | |
| 6,939,358 B2 | 9/2005 | Palacios et al. | |
| 6,946,196 B2 | 9/2005 | Foss | |
| 6,959,851 B2 | 11/2005 | Heinrich | |
| 7,060,087 B2 | 6/2006 | DiMatteo et al. | |
| 7,087,065 B2 | 8/2006 | Ulmsten et al. | |
| 7,108,701 B2 | 9/2006 | Evens et al. | |
| 7,128,253 B2 | 10/2006 | Mastri et al. | |
| 7,128,748 B2 | 10/2006 | Mooradian et al. | |
| 7,134,438 B2 | 11/2006 | Makower et al. | |
| 7,141,055 B2 | 11/2006 | Abrams et al. | |
| 7,147,138 B2 | 12/2006 | Shelton, IV | |
| 7,160,299 B2 | 1/2007 | Baily | |
| 7,232,449 B2 | 6/2007 | Sharkawy et al. | |
| 7,241,300 B2 | 7/2007 | Sharkawy et al. | |
| 7,307,031 B2 | 12/2007 | Carroll et al. | |
| 7,311,720 B2 | 12/2007 | Mueller et al. | |
| 7,334,717 B2 | 2/2008 | Rethy et al. | |
| 7,377,928 B2 | 5/2008 | Zubik et al. | |
| 7,434,717 B2 | 10/2008 | Shelton, IV et al. | |
| 7,438,209 B1 | 10/2008 | Hess et al. | |
| 7,547,312 B2 * | 6/2009 | Bauman et al. | 606/151 |
| 7,559,937 B2 | 7/2009 | de la Torre et al. | |
| 7,571,845 B2 | 8/2009 | Viola | |
| 7,594,921 B2 | 9/2009 | Browning | |
| 7,604,151 B2 | 10/2009 | Hess et al. | |
| 7,665,646 B2 | 2/2010 | Prommersberger | |
| 7,666,198 B2 | 2/2010 | Suyker et al. | |
| 7,669,747 B2 | 3/2010 | Weisenburgh, II et al. | |
| 7,717,313 B2 | 5/2010 | Bettuchi et al. | |
| 7,722,642 B2 | 5/2010 | Williamson, IV | |
| 7,744,627 B2 | 6/2010 | Orban, III et al. | |
| 7,776,060 B2 | 8/2010 | Mooradian | |
| 7,793,813 B2 | 9/2010 | Bettuchi | |
| 7,799,026 B2 | 9/2010 | Schechter et al. | |
| 7,823,592 B2 | 11/2010 | Bettuchi et al. | |
| 7,824,420 B2 | 11/2010 | Eldridge et al. | |
| 7,845,533 B2 | 12/2010 | Marczyk et al. | |
| 7,845,536 B2 | 12/2010 | Viola et al. | |
| 7,846,149 B2 | 12/2010 | Jankowski | |
| 7,892,247 B2 | 2/2011 | Conston et al. | |
| 7,909,224 B2 | 3/2011 | Prommersberger | |
| 7,909,837 B2 | 3/2011 | Crows et al. | |
| 7,938,307 B2 | 5/2011 | Bettuchi et al. | |
| 7,942,890 B2 | 5/2011 | D'Agostino et al. | |
| 7,950,561 B2 | 5/2011 | Aranyi | |
| 7,951,166 B2 | 5/2011 | Orban | |
| 7,967,179 B2 * | 6/2011 | Olson | A61B 17/07207 227/175.1 |

(56) References Cited

U.S. PATENT DOCUMENTS

| | | |
|---|---|---|
| 7,988,027 B2 | 8/2011 | Olson |
| 8,011,550 B2 | 9/2011 | Aranyi |
| 8,016,177 B2 * | 9/2011 | Bettuchi .......... A61B 17/07207 227/175.1 |
| 8,016,178 B2 | 9/2011 | Olson |
| 8,028,883 B2 | 10/2011 | Stopek |
| 8,062,330 B2 | 11/2011 | Prommersberger |
| 8,083,119 B2 | 12/2011 | Prommersberger |
| 8,123,766 B2 | 2/2012 | Bauman |
| 8,123,767 B2 | 2/2012 | Bauman |
| 8,146,791 B2 | 4/2012 | Bettuchi |
| 8,157,149 B2 | 4/2012 | Olson |
| 8,157,151 B2 | 4/2012 | Ingmanson |
| 8,167,895 B2 | 5/2012 | D'Agostino |
| 8,178,746 B2 | 5/2012 | Hildeberg et al. |
| 8,192,460 B2 | 6/2012 | Orban |
| 8,210,414 B2 | 7/2012 | Bettuchi |
| 8,225,799 B2 | 7/2012 | Bettuchi |
| 8,225,981 B2 | 7/2012 | Criscuolo et al. |
| 8,231,043 B2 | 7/2012 | Tarinelli |
| 8,235,273 B2 | 8/2012 | Olson |
| 8,245,901 B2 | 8/2012 | Stopek |
| 8,256,654 B2 | 9/2012 | Bettuchi |
| 8,257,391 B2 | 9/2012 | Orban |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi |
| 8,308,046 B2 | 11/2012 | Prommersberger |
| 8,312,885 B2 | 11/2012 | Bettuchi |
| 8,313,014 B2 | 11/2012 | Bettuchi |
| 8,348,126 B2 | 1/2013 | Olson |
| 8,348,130 B2 * | 1/2013 | Shah ................ A61B 17/07207 227/179.1 |
| 8,365,972 B2 | 2/2013 | Aranyi et al. |
| 8,371,491 B2 | 2/2013 | Huitema |
| 8,371,492 B2 | 2/2013 | Aranyi |
| 8,371,493 B2 | 2/2013 | Aranyi |
| 8,393,514 B2 | 3/2013 | Shelton, IV |
| 8,408,440 B2 | 4/2013 | Olson |
| 8,413,869 B2 | 4/2013 | Heinrich |
| 8,413,871 B2 | 4/2013 | Racenet |
| 8,424,742 B2 | 4/2013 | Bettuchi |
| 8,453,652 B2 | 6/2013 | Stopek |
| 8,453,909 B2 | 6/2013 | Olson |
| 8,453,910 B2 | 6/2013 | Bettuchi |
| 8,464,925 B2 | 6/2013 | Hull et al. |
| 8,474,677 B2 | 7/2013 | Woodard, Jr. |
| 8,479,968 B2 | 7/2013 | Hodgkinson |
| 8,485,414 B2 | 7/2013 | Criscuolo et al. |
| 8,496,683 B2 | 7/2013 | Prommersberger |
| 8,511,533 B2 | 8/2013 | Viola |
| 8,512,402 B2 | 8/2013 | Marczyk |
| 8,529,600 B2 | 9/2013 | Woodard, Jr. |
| 8,540,131 B2 | 9/2013 | Swayze |
| 8,551,138 B2 | 10/2013 | Orban |
| 8,556,918 B2 | 10/2013 | Bauman |
| 8,561,873 B2 | 10/2013 | Ingmanson |
| 8,584,920 B2 * | 11/2013 | Hodgkinson ...... A61B 17/0682 227/175.1 |
| 8,590,762 B2 | 11/2013 | Hess |
| 8,616,430 B2 | 12/2013 | Prommersberger |
| 8,631,989 B2 | 1/2014 | Aranyi |
| 8,646,674 B2 | 2/2014 | Schulte et al. |
| 8,668,129 B2 | 3/2014 | Olson |
| 8,684,250 B2 | 4/2014 | Bettuchi |
| 8,721,703 B2 | 5/2014 | Fowler |
| 8,757,466 B2 | 6/2014 | Olson |
| 8,789,737 B2 | 7/2014 | Hodgkinson |
| 8,820,606 B2 | 9/2014 | Hodgkinson |
| 8,920,444 B2 | 12/2014 | Hiles et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 2002/0028243 A1 | 3/2002 | Masters |
| 2002/0091397 A1 | 7/2002 | Chen |
| 2003/0065345 A1 | 4/2003 | Weadock |
| 2003/0083676 A1 | 5/2003 | Wallace |
| 2003/0120284 A1 | 6/2003 | Palacios et al. |
| 2003/0181927 A1 | 9/2003 | Wallace |
| 2003/0183671 A1 | 10/2003 | Mooradian et al. |
| 2003/0208231 A1 | 11/2003 | Williamson, IV et al. |
| 2004/0107006 A1 | 6/2004 | Francis et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2005/0184121 A1 * | 8/2005 | Heinrich ............ A61B 17/0686 227/175.1 |
| 2005/0228446 A1 * | 10/2005 | Mooradian .......... A61B 17/115 606/215 |
| 2006/0004388 A1 * | 1/2006 | Whayne et al. ................ 606/151 |
| 2006/0004407 A1 | 1/2006 | Hiles et al. |
| 2006/0135992 A1 | 6/2006 | Bettuchi |
| 2006/0173470 A1 | 8/2006 | Oray et al. |
| 2006/0178683 A1 | 8/2006 | Shimoji et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 * | 1/2009 | Prommersberger et al. ........................ 227/176.1 |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 * | 4/2009 | Eskaros et al. ............. 227/175.1 |
| 2009/0095792 A1 | 4/2009 | Bettuchi |
| 2009/0120994 A1 | 5/2009 | Murray et al. |

(56) References Cited

U.S. PATENT DOCUMENTS

| | | |
|---|---|---|
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1* | 8/2009 | Huitema .......... A61B 17/07207 227/176.1 |
| 2009/0218384 A1* | 9/2009 | Aranyi ............. A61B 17/07207 227/176.1 |
| 2009/0277944 A9 | 11/2009 | Dalessandro et al. |
| 2009/0277947 A1* | 11/2009 | Viola ............... A61B 17/07207 227/176.1 |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0174253 A1* | 7/2010 | Cline et al. .................... 604/328 |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2010/0331880 A1 | 12/2010 | Stopek |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2011/0215132 A1 | 9/2011 | Aranyi |
| 2012/0074199 A1 | 3/2012 | Olson |
| 2012/0080336 A1 | 4/2012 | Shelton |
| 2012/0080338 A1* | 4/2012 | Shelton, IV ...... A61B 17/00491 206/339 |
| 2012/0083723 A1 | 4/2012 | Vitaris et al. |
| 2012/0187179 A1 | 7/2012 | Gleiman |
| 2012/0197272 A1 | 8/2012 | Oray et al. |
| 2012/0241499 A1 | 9/2012 | Baxter |
| 2012/0273547 A1 | 11/2012 | Hodgkinson et al. |
| 2013/0037596 A1 | 2/2013 | Bear et al. |
| 2013/0105548 A1 | 5/2013 | Hodgkinson |
| 2013/0105553 A1 | 5/2013 | Racenet |
| 2013/0112732 A1 | 5/2013 | Aranyi |
| 2013/0112733 A1 | 5/2013 | Aranyi |
| 2013/0146641 A1 | 6/2013 | Shelton |
| 2013/0153633 A1 | 6/2013 | Casasanta |
| 2013/0153634 A1 | 6/2013 | Carter |
| 2013/0153635 A1 | 6/2013 | Hodgkinson |
| 2013/0153636 A1 | 6/2013 | Shelton |
| 2013/0153638 A1 | 6/2013 | Carter |
| 2013/0153639 A1 | 6/2013 | Hodgkinson |
| 2013/0153641 A1 | 6/2013 | Shelton |
| 2013/0161374 A1 | 6/2013 | Swayze |
| 2013/0181031 A1 | 7/2013 | Olson |
| 2013/0193186 A1 | 8/2013 | Racenet |
| 2013/0193190 A1 | 8/2013 | Carter |
| 2013/0193191 A1 | 8/2013 | Stevenson |
| 2013/0193192 A1 | 8/2013 | Casasanta |
| 2013/0209659 A1 | 8/2013 | Racenet |
| 2013/0214030 A1* | 8/2013 | Aronhalt ............ A61B 17/068 227/176.1 |
| 2013/0221062 A1* | 8/2013 | Hodgkinson ........ A61B 17/072 227/176.1 |
| 2013/0240600 A1 | 9/2013 | Bettuchi |
| 2013/0240601 A1 | 9/2013 | Bettuchi |
| 2013/0240602 A1 | 9/2013 | Stopek |
| 2013/0256380 A1 | 10/2013 | Schmid et al. |
| 2013/0277411 A1 | 10/2013 | Hodgkinson |
| 2013/0306707 A1 | 11/2013 | Viola |
| 2013/0310873 A1 | 11/2013 | Stopek et al. |
| 2013/0327807 A1 | 12/2013 | Olson |
| 2014/0012317 A1 | 1/2014 | Orban |
| 2014/0021242 A1 | 1/2014 | Hodgkinson |
| 2014/0027490 A1 | 1/2014 | Marczyk |
| 2014/0034704 A1 | 2/2014 | Ingmanson |
| 2014/0048580 A1* | 2/2014 | Merchant ............ A61B 17/064 227/176.1 |
| 2014/0061280 A1 | 3/2014 | Ingmanson |
| 2014/0061281 A1 | 3/2014 | Hodgkinson |
| 2014/0084042 A1 | 3/2014 | Stopek |
| 2014/0097224 A1 | 4/2014 | Prior |
| 2014/0117066 A1 | 5/2014 | Aranyi |
| 2014/0130330 A1 | 5/2014 | Olson |
| 2014/0131418 A1 | 5/2014 | Kostrzewski |
| 2014/0131419 A1 | 5/2014 | Bettuchi |
| 2014/0138423 A1 | 5/2014 | Whitfield |
| 2014/0151431 A1 | 6/2014 | Hodgkinson |
| 2014/0155916 A1 | 6/2014 | Hodgkinson |
| 2014/0158742 A1 | 6/2014 | Stopek |
| 2014/0166721 A1* | 6/2014 | Stevenson ........ A61B 17/07292 227/176.1 |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1* | 8/2014 | Hodgkinson .... A61B 17/07292 227/180.1 |
| 2015/0122872 A1 | 5/2015 | Olson et al. |
| 2015/0164503 A1 | 6/2015 | Stevenson et al. |
| 2015/0164506 A1 | 6/2015 | Carter et al. |
| 2015/0164507 A1 | 6/2015 | Carter et al. |
| 2015/0196297 A1 | 7/2015 | Stopek et al. |
| 2015/0209033 A1 | 7/2015 | Hodgkinson |
| 2015/0209045 A1 | 7/2015 | Hodgkinson et al. |
| 2015/0209048 A1 | 7/2015 | Carter et al. |

FOREIGN PATENT DOCUMENTS

| | | |
|---|---|---|
| CN | 101332110 A | 12/2008 |
| DE | 1 99 24 311 A1 | 11/2000 |
| EP | 0 594 148 A1 | 4/1994 |
| EP | 0 327 022 B1 | 4/1995 |
| EP | 0 667 119 A1 | 8/1995 |
| EP | 1 064 883 A1 | 1/2001 |
| EP | 1 256 317 A2 | 11/2002 |
| EP | 1 256 318 | 11/2002 |
| EP | 1 520 525 A1 | 4/2005 |
| EP | 1 621 141 A2 | 2/2006 |
| EP | 1 702 570 A2 | 9/2006 |
| EP | 1 759 640 A2 | 3/2007 |
| EP | 1 815 804 A2 | 8/2007 |
| EP | 1 825 820 | 8/2007 |
| EP | 1 929 958 | 6/2008 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 039 308 A2 | 3/2009 |
| EP | 2 090 231 | 8/2009 |
| EP | 2 090 244 | 8/2009 |
| EP | 2 090 252 | 8/2009 |
| EP | 2 163 211 A2 | 3/2010 |
| EP | 2 189 121 A1 | 5/2010 |
| EP | 2 198 787 A1 | 6/2010 |
| EP | 2 236 098 A2 | 10/2010 |
| EP | 2 236 099 | 10/2010 |
| EP | 2 258 282 A2 | 12/2010 |
| EP | 2 311 386 | 4/2011 |
| EP | 2 436 348 | 4/2012 |
| EP | 2 462 880 | 6/2012 |
| EP | 2 497 431 A1 | 9/2012 |
| EP | 2 517 637 | 10/2012 |
| EP | 2 586 380 | 5/2013 |
| EP | 2 604 195 | 6/2013 |
| EP | 2 604 197 | 6/2013 |
| EP | 2 620 106 | 7/2013 |

(56) References Cited

FOREIGN PATENT DOCUMENTS

| | | |
|---|---|---|
| EP | 2 630 922 | 8/2013 |
| EP | 2 644 125 | 10/2013 |
| JP | 2000-166933 | 6/2000 |
| JP | 2002-202213 | 7/2002 |
| JP | 07-124166 | 5/2007 |
| JP | 2007-124166 | 5/2007 |
| WO | WO 90/05489 A1 | 5/1990 |
| WO | WO 95/16221 | 6/1995 |
| WO | WO 96/22055 A1 | 7/1996 |
| WO | WO 97/01989 A1 | 1/1997 |
| WO | WO 97/13463 A1 | 4/1997 |
| WO | WO 98/17180 A1 | 4/1998 |
| WO | WO 99/45849 A1 | 9/1999 |
| WO | WO 03/082126 A1 | 10/2003 |
| WO | WO 03/088845 | 10/2003 |
| WO | WO 03/094743 | 11/2003 |
| WO | WO 03/105698 A2 | 12/2003 |
| WO | WO 2005/079675 | 9/2005 |
| WO | WO 2006/023578 A2 | 3/2006 |
| WO | WO 2006/044490 A2 | 4/2006 |
| WO | WO 2006/083748 A1 | 8/2006 |
| WO | WO 2007/121579 A1 | 11/2007 |
| WO | WO 2008/057281 A2 | 5/2008 |
| WO | WO 2008/109125 A1 | 9/2008 |
| WO | WO 2010/075298 A2 | 7/2010 |
| WO | WO 2011/143183 A2 | 11/2011 |
| WO | WO 2012/044848 A1 | 4/2012 |

OTHER PUBLICATIONS

Extended European Search Report corresponding to EP 13 19 5919.9, completed Feb. 10, 2014 and mailed Mar. 3, 2014; (7 pp).
Extended European Search Report corresponding to EP 13 19 2123.1, completed Jan. 30, 2014 and mailed Feb. 10, 2014; (8 pp).
Extended European Search Report corresponding to EP 13 19 6816.6, completed Mar. 28, 2014 and mailed Apr. 9, 2014; (9 pp).
Extended European Search Report corresponding to EP 13 19 4995.0, completed Jun. 5, 2014 and mailed Jun. 16, 2014; (5 pp).
Extended European Search Report corresponding to EP 13 19 5019.8, completed Mar. 14, 2014 and mailed Mar. 24, 2014; (7 pp).
Extended European Search Report corresponding to EP 13 19 2111.6, completed Feb. 13, 2014 and mailed Feb. 27, 2014; (10 pp).
Extended European Search Report corresponding to EP 14 15 6342.9, completed Jul. 22, 2014 and mailed Jul. 29, 2014; (8 pp).
Extended European Search Report corresponding to EP 14 15 7195.0, completed Jun. 5, 2014 and mailed Jun. 18, 2014; (9 pp).
Extended European Search Report corresponding to EP 13180373.6, completed Oct. 31, 2013 and mailed Nov. 13, 2013; (7 pp).
Extended European Search Report corresponding to EP 13 17 7437.4, completed Sep. 11, 2013 and mailed Sep. 19, 2013; (6 pp).
Extended European Search Report corresponding to EP 13 17 7441.6, completed Sep. 11, 2013 and mailed Sep. 19, 2013; (6 pp).
Extended European Search Report corresponding to EP 07 86 1534.1, completed Sep. 20, 2013 and mailed Sep. 30, 2013; (5 pp).
Extended European Search Report corresponding to EP 13 18 3876.5, completed Oct. 14, 2013 and mailed Oct. 24, 2013; (5 pp).
Extended European Search Report corresponding to EP 13 17 1856.1, completed Oct. 29, 2013 and mailed Nov. 7, 2013; (8 pp).
Extended European Search Report corresponding to EP 13 18 0881.8, completed Nov. 5, 2013 and mailed Nov. 14, 2013; (6 pp).
Extended European Search Report corresponding to EP 13 17 6895.4, completed Nov. 29, 2013 and mailed Dec. 12, 2013; (5 pp).
Extended European Search Report corresponding to EP 13 18 2911.1, completed Dec. 2, 2013 and mailed Dec. 16, 2013; (8 pp).
Extended European Search Report corresponding to EP 10 25 1795.0, completed Dec. 11, 2013 and mailed Dec. 20, 2013; (6 pp).
Extended European Search Report corresponding to EP 13 18 7911.6, completed Jan. 22, 2014 and mailed Jan. 31, 2014; (8 pp).
Extended European Search Report corresponding to EP 13 19 7958.5, completed Apr. 4, 2014 and mailed Apr. 15, 2014; (8 pp).
Extended European Search Report corresponding to EP No. 12 19 1035.0, completed Jan. 11, 2013 and mailed Jan. 18, 2013; 7 pages.
Extended European Search Report corresponding to EP No. 12 18 6175.1, completed Jan. 15, 2013 and mailed Jan. 23, 2013; 7 pages.
Extended European Search Report corresponding to EP No. 12 19 1114.3, completed Jan. 23, 2013 and mailed Jan. 31, 2013; 10 pages.
Extended European Search Report corresponding to EP No. 12 19 2224.9, completed Mar. 14, 2013 and mailed Mar. 26, 2013; 8 pages.
Extended European Search Report corresponding to EP No. 12 19 6911.7, completed Apr. 18, 2013 and mailed Apr. 24, 2013; 8 pages.
Extended European Search Report corresponding to EP 12 19 1035.0, completed Jan. 11, 2013 and mailed Jan. 18, 2013; 7 pages.
Extended European Search Report corresponding to EP 12 19 6904.2, completed Mar. 28, 2013 and mailed Jul. 26, 2013; 8 pages.
Extended European Search Report corresponding to EP 12 19 8749.9, completed May 21, 2013 and mailed May 31, 2013; 8 pages.
Extended European Search Report corresponding to EP 07 00 5842.5, completed May 13, 2013 and mailed May 29, 2013; 7 pages.
Extended European Search Report corresponding to EP 12 19 8776.2, completed May 16, 2013 and mailed May 27, 2013; 8 pages.
Extended European Search Report corresponding to EP 13 15 6297.7, completed Jun. 4, 2013 and mailed Jun. 13, 2013; 7 pages.
Extended European Search Report corresponding to EP 13 17 3985.6, completed Aug. 19, 2013 and mailed Aug. 28, 2013; 6 pages.
Extended European Search Report corresponding to EP 13 17 3986.4, completed Aug. 20, 2013 and mailed Aug. 29, 2013; 7 pages.
International Search Report corresponding to European Application No. EP 05 02 2585.3, completed on Jan. 25, 2006 and mailed on Feb. 3, 2006; 4 pages.
International Search Report corresponding to European Application No. EP 06 00 4598, completed on Jun. 22, 2006; 2 pages.
International Search Report corresponding to European Application No. EP 06 01 6962.0, completed on Jan. 3, 2007 and mailed on Jan. 11, 2007; 10 pages.
International Search Report corresponding to International Application No. PCT/US05/36740, completed on Feb. 20, 2007 and mailed on Mar. 23, 2007; 8 pages.
International Search Report corresponding to International Application No. PCT/US2007/022713, completed on Apr. 21, 2008 and mailed on May 15, 2008; 1 page.
International Search Report corresponding to International Application No. PCT/US2008/002981, completed on Jun. 9, 2008 and mailed on Jun. 26, 2008; 2 pages.
International Search Report corresponding to European Application No. EP 08 25 1779, completed on Jul. 14, 2008 and mailed on Jul. 23, 2008; 5 pages.
International Search Report corresponding to European Application No. EP 08 25 1989.3, completed on Mar. 11, 2010 and mailed on Mar. 24, 2010; 6 pages.
International Search Report corresponding to European Application No. EP 10 25 0639.1, completed on Jun. 17, 2010 and mailed on Jun. 28, 2010; 7 pages.
International Search Report corresponding to European Application No. EP 10 25 0715.9, completed on Jun. 30, 2010 and mailed on Jul. 20, 2010; 3 pages.
International Search Report corresponding to European Application No. EP 05 80 4382.9, completed on Oct. 5, 2010 and mailed on Oct. 12, 2010; 3 pages.
International Search Report corresponding to European Application No. EP 10 25 1437.9, completed on Nov. 22, 2010 and mailed on Dec. 16, 2010; 3 pages.
International Search Report corresponding to European Application No. EP 09 25 2897.5, completed on Feb. 7, 2011 and mailed on Feb. 15, 2011; 3 pages.
International Search Report corresponding to European Application No. EP 10 25 0642.5, completed on Mar. 25, 2011 and mailed on Apr. 4, 2011; 4 pages.
International Search Report corresponding to European Application No. EP 11 18 8309.6, completed on Dec. 15, 2011 and mailed on Jan. 12, 2012; 3 pages.
International Search Report corresponding to European Application No. EP 12 15 2229.6, completed on Feb. 23, 2012 and mailed on Mar. 1, 2012; 4 pages.

(56) References Cited

OTHER PUBLICATIONS

International Search Report corresponding to European Application No. EP 12 15 0511.9, completed on Apr. 16, 2012 and mailed on Apr. 24, 2012; 7 pages.
International Search Report corresponding to European Application No. EP 12 15 2541.4, completed on Apr. 23, 2012 and mailed on May 3, 2012; 10 pages.
International Search Report corresponding to European Application No. EP 12 16 5609.4, completed on Jul. 5, 2012 and mailed on Jul. 13, 2012; 8 pages.
International Search Report corresponding to European Application No. EP 12 15 8861.0, completed on Jul. 17, 2012 and mailed on Jul. 24, 2012; 9 pages.
International Search Report corresponding to European Application No. EP 12 16 5878.5, completed on Jul. 24, 2012 and mailed on Aug. 6, 2012; 8 pages.
European Office Action corresponding to EP 13 180 373.6 dated Jun. 19, 2015; 4 pp.
European Office Action corresponding to counterpart Int'l Appln No. EP 12 198 776.2 dated Apr. 7, 2015.
European Office Action corresponding to counterpart Int'l Appln No. EP 13 156 297.7 dated Apr. 10, 2015.
Australian Examination Report No. 1 corresponding to counterpart Int'l Appln No. AU 2011250822 dated May 18, 2015.
European Office Action corresponding to counterpart Int'l Appln No. EP 12 186 175.1 dated Jun. 1, 2015.
Chinese Office Action corresponding to counterpart Int'l Appln No. CN 201010517292.8 dated Jun. 2, 2015.
Extended European Search Report corresponding to counterpart Int'l Appln No. EP 14 17 4814.5 dated Jun. 9, 2015.
Australian Examination Report No. 1 corresponding to counterpart Int'l Appln No. AU 2014200584 dated Jun. 15, 2015.
European Office Action corresponding to counterpart Int'l Appln No. EP 13 180 881.8 dated Jun. 19, 2015.
European Office Action corresponding to counterpart Int'l Appln No. EP 14 157 195.0 dated Jul. 2, 2015.
Extended European Search Report corresponding to counterpart Int'l Appln No. EP 12 19 6902.6 dated Aug. 6, 2015.
Extended European Search Report corresponding to counterpart Int'l Appln No. EP 14 15 2060.1 dated Aug. 14, 2015.
Chinese Office Action corresponding to counterpart Int'l Appln No. CN 201210129787.2 dated Aug. 24, 2015.

\* cited by examiner

Fig. 11
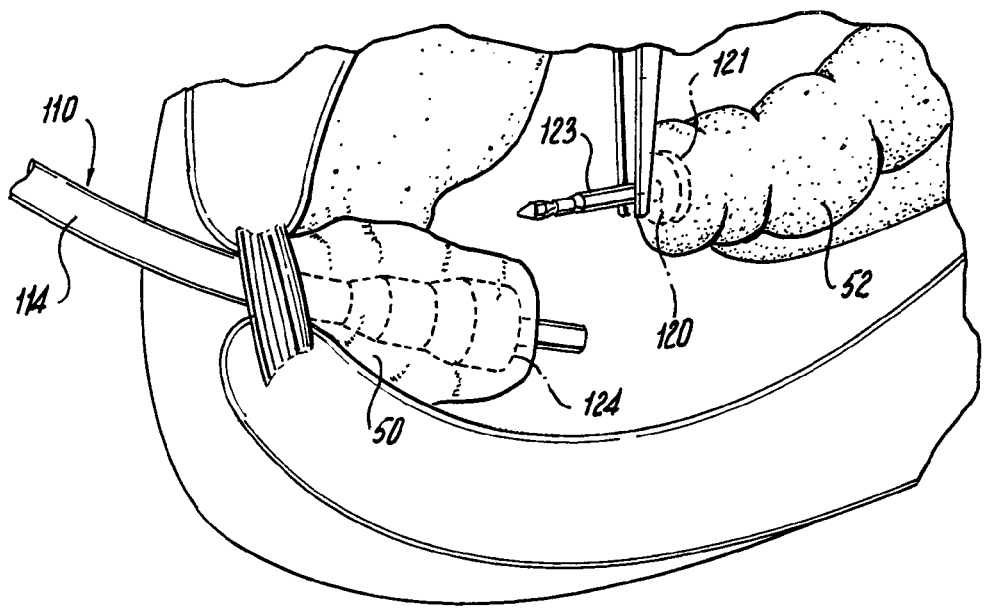
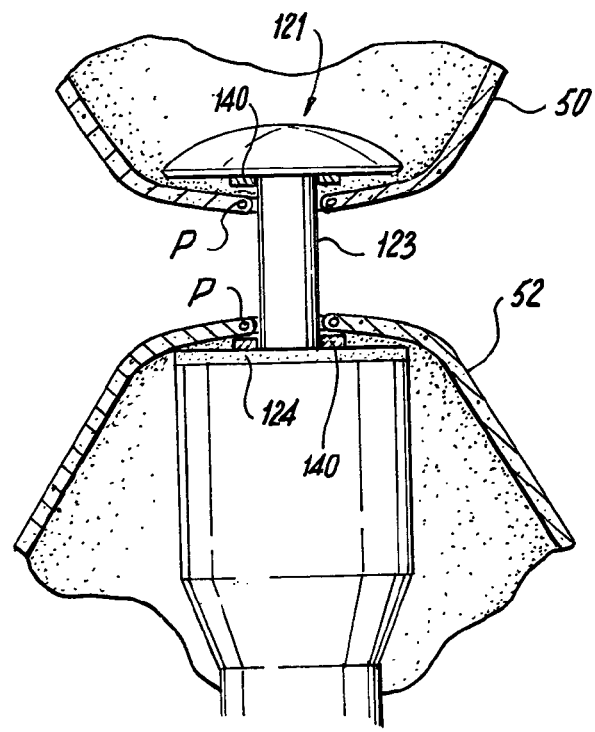
Fig. 12

BUTTRESS ATTACHMENT TO THE CARTRIDGE SURFACE

CROSS-REFERENCE TO RELATED APPLIACTIONS

The present application is a Continuation-in-Part Application which claims the benefit of and priority to U.S. patent application Ser. No. 13/586,261, filed on Aug. 15, 2012, which is a Continuation-in-Part Application which claims the benefit of and priority to U.S. patent application Ser. No. 13/325,481, filed Dec. 14, 2011, the entire disclosure of each of which is hereby incorporated by reference herein.

BACKGROUND

1. Technical Field

The present disclosure relates to surgical stapling apparatus including surgical buttresses which can be releasably attached to the surgical stapling apparatus, and in particular, to surgical stapling apparatus having adhesive member disposed on a tissue contacting surface of the surgical stapling apparatus to join the surgical buttresses thereto.

2. Background of Related Art

Surgical stapling apparatus are employed by surgeons to sequentially or simultaneously apply one or more rows of fasteners, e.g., staples or two-part fasteners, to body tissue for the purpose of joining segments of body tissue together. Such apparatus generally include a pair of jaws or finger-like structures between which the body tissue to be joined is placed. When the stapling apparatus is actuated, or "fired", longitudinally moving firing bars contact staple drive members in one of the jaws. The staple drive members push the surgical staples through the body tissue and into an anvil in the opposite jaw which forms the staples. If tissue is to be removed or separated, a knife blade can be provided in the jaws of the apparatus to cut the tissue between the lines of staples.

A number of surgical stapling apparatus rely on a knife blade cutting off some portion of the surgical buttress to affect release. These methods typically employ a secondary material or mounting structure in addition to the surgical buttress (e.g., sutures) to provide attachment of the surgical buttress to the surgical stapling apparatus. Typically, firing forces are increased with each material that must be transected by the knife blade in order to release the surgical buttress.

It would be desirable to provide a surgical buttress that may be releasably secured to a surgical stapling apparatus without the need for a secondary material or mounting structure, and without the need for a knife blade to cut the buttress and/or mounting structure to release the surgical buttress from the surgical stapling apparatus, thereby resulting in the use of fewer materials and lower firing forces.

SUMMARY

According to one aspect of the present disclosure, an end effector assembly for use with a surgical stapler wherein the end effector comprises a staple cartridge having a tissue contacting surface defining a central longitudinal slot and an anvil plate having a tissue contacting surface defining a central longitudinal slot. A surgical buttress is releasbly disposed on the tissue contacting surfaces of each of the staple cartridge and anvil plate. An adhesive tape is disposed over the central longitudinal slot of each of the staple cartridge and anvil plate and configured retain the respective surgical buttress atop the respective tissue contacting surface. Preferably, the surgical buttress is laser welded to the adhesive tape.

The adhesive tape is secured to the tissue contacting surfaces of each of the staple cartridge and anvil plate surrounding the edges of the respective central longitudinal slots. Additionally, the adhesive tape extends longitudinally between a proximal end and a distal end of the tissue contacting surfaces of each of the staple cartridge and anvil plate.

According to another aspect of the present disclosure, a staple cartridge for use with a surgical stapling apparatus wherein the staple cartridge comprises a cartridge body including a tissue contacting surface defining a plurality of staple retaining slots and having a central longitudinal slot and a staple disposed within each staple retaining slot of the cartridge body. A surgical buttress is releasbly disposed on the tissue contacting surfaces of the cartridge body. An adhesive tape is disposed over the central longitudinal slot of the cartridge body and configured to retain the surgical buttress atop the tissue contacting surface of the cartridge body. Preferably, the surgical buttress is laser welded to the adhesive tape.

The adhesive tape is secured to the tissue contacting surface of the cartridge body surrounding the edges of the central longitudinal slot. Additionally, the adhesive tape extends longitudinally between a proximal end and a distal end of the tissue contacting surface of the cartridge body.

According to another aspect of the present disclosure, a surgical stapling apparatus wherein the surgical stapling apparatus comprises a housing and an end effector being secured to the housing having a staple cartridge assembly having a tissue contacting surface and an anvil assembly having a tissue contacting surface, each of the staple cartridge assembly and anvil assembly having a central longitudinal slot. A surgical buttress is releasbly disposed on the tissue contacting surfaces of each of the staple cartridge assembly and anvil assembly. An adhesive tape is disposed over the central longitudinal slot of each of the staple cartridge assembly and anvil assembly and configured retain the respective surgical buttress atop the respective tissue contacting surface. Preferably, the surgical buttress is laser welded to the adhesive tape.

BRIEF DESCRIPTION OF THE DRAWINGS

Various embodiments of the presently disclosed interlocking buttress retention systems are disclosed herein with reference to the drawings, wherein:

FIG. 11 is perspective view of an intestinal area of a patient, illustrating a method of positioning an anvil rod and staple cartridge assembly of the surgical stapling apparatus of FIGS. 9A, 9B, and 10 within the intestinal area; and FIG. 12 is a schematic perspective view of the intestinal area of FIG. 11, illustrating the anvil rod mounted to the surgical stapling apparatus.

DETAILED DESCRIPTION OF THE EMBODIMENTS

Figure 1:
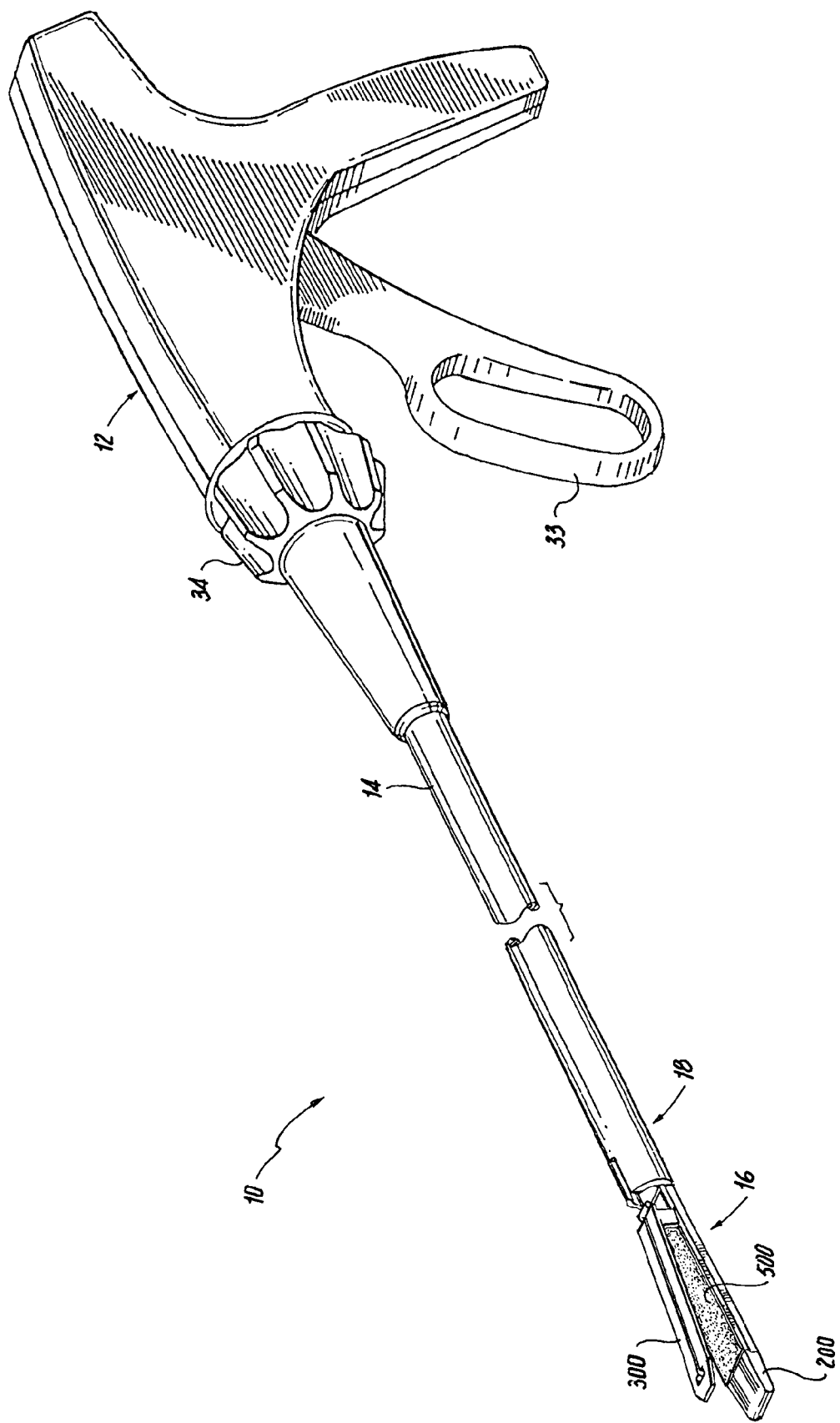
FIG. 1 is a perspective view of a surgical stapling apparatus according to an embodiment of the present disclosure.

Various exemplary embodiments of the present disclosure are discussed herein below in terms of buttresses for use with surgical stapling apparatus. The buttresses described herein may be used in sealing a wound by approximating the edges of wound tissue between a staple cartridge and an anvil plate of a surgical stapling apparatus which contains at least one surgical buttress. The at least one surgical buttress is joined to the surgical stapling apparatus by a strategically placed adhesive member, which can be an adhesive tape. The adhesive member is placed adjacent a central longitudinal slot and positioned between a tissue contacting surface of each of the staple cartridge and anvil plate and the least one surgical buttress. Firing of the surgical stapling apparatus forces legs of at least one staple to pass through an opening on the staple cartridge, the tissue, and the openings on the anvil plate to secure the surgical buttress to the tissue, to secure the adjoining tissue to one another. The buttress can help seal the tissue, and support the tissue. The firing force of the staple impacts the adhesive member to break the bond between the adhesive member and the surgical buttress thereby releasing the surgical buttress from the tissue contacting surface. As a knife blade translates distally within the central longitudinal slot, the adhesive tape is cut and fully releases the surgical buttress from the tissue contacting surface. Thus, the present disclosure describes surgical buttresses, surgical stapling apparatus supporting said surgical buttresses, and methods and mechanisms for using the same.

It should be understood that a variety of surgical stapling apparatus may be utilized with a surgical buttress of the present disclosure. For example, linear stapler configurations may be utilized, such as, for example those including Duet TRS™ reloads and staplers with Tri-Staple™ technology, available through Covidien, which maintain a principal place of business at 555 Long Wharf Drive, North Haven, Conn. 06511, and transverse anastomosis staplers, such as, for example, EEA™, CEEA™, GIA™, EndoGIA™, and TA™ staplers, also available through Covidien. It should also be appreciated that the principles of the present disclosure are equally applicable to surgical staplers having alternate configurations, such as, for example, end-to-end anastomosis staplers having a circular cartridge and anvil (see, e.g., commonly owned U.S. Pat. No. 5,915,616, entitled "Surgical Fastener Applying Apparatus," the entire content of which is incorporated herein by this reference); laparoscopic staplers (see, e.g., commonly owned U.S. Pat. Nos. 6,330,965 and 6,241,139, each entitled "Surgical Stapling Apparatus," the entire contents of each of which being incorporated herein by this reference); and transverse anastomosis staplers (see, e.g., commonly owned U.S. Pat. Nos. 5,964,394 and 7,334,717, each entitled "Surgical Fastener Applying Apparatus", the entire contents of each of which being incorporated herein by this reference).

Embodiments of the presently disclosed surgical buttress and surgical stapling apparatus will now be described in detail with reference to the drawing figures wherein like reference numerals identify similar or identical elements. In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human subject or other animal, and the term "clinician" should be understood as referring to a doctor, nurse, or other care provider and may include support personnel.

Referring now to FIG. 1, there is disclosed an exemplary surgical stapling apparatus or surgical stapler 10 for use in stapling tissue and applying a buttress material or surgical buttress to the tissue. A further example of this type of surgical stapling instrument is disclosed in U.S. Pat. No. 7,128,253, the entire disclosure of which is incorporated by reference herein. The surgical stapling instrument can have a removable and replaceable loading unit that includes the cartridge assembly and anvil assembly, a surgical stapling instrument with a removable and replaceable cartridge assembly, or both. The surgical stapling instrument may have a manually driven handle assembly or a handle assembly that is powered by electrical motor, pressurized gas or other fluid, etc.

Surgical stapling apparatus 10 generally includes a handle 12 having an elongate tubular member 14 extending distally from handle 12. An end effector assembly 16 is mounted on a distal end 18 of elongate tubular member 14. End effector assembly 16 includes a first jaw or staple cartridge assembly 200 configured to receive a staple cartridge 32 therein and a second jaw or anvil assembly 300. End effector assembly 16 may be permanently affixed to elongate tubular member 14 or may be detachable and thus replaceable with a new end effector assembly 16. One of staple cartridge assembly 200 and anvil assembly 300 is movably mounted at distal end 18 of end effector assembly 16, and is movable between an open position spaced apart from one another to a closed position substantially adjacent to one another. Anvil assembly 300 supports an anvil plate 302 and is fabricated from a material appropriate to surgical uses, such as a metal material including and not limited to stainless steel, titanium, titanium alloy, and the like. At least a tissue contacting surface of staple cartridge 32 is fabricated from a material other than metal, including and not limited to plastic, thermoplastic, resin, polycarbonate, and the like.

Surgical stapling apparatus 10 further includes a trigger 33, as seen in FIG. 1, movably mounted on handle 12. Actuation of trigger 33 initially operates to move first jaw and second jaw between the open and the closed positions and simultaneously actuates surgical stapling apparatus 10 to apply lines of staples to tissue. In order to properly orient end effector assembly 16 relative to the tissue to be stapled, surgical stapling apparatus 10 is additionally provided with a rotation knob 34 mounted on handle 12. Rotation of rotation knob 34 relative to handle 12 rotates elongate tubular member 14 and end effector assembly 16 relative to handle 12 so as to properly orient end effector assembly 16 relative to the tissue to be stapled. The surgical stapling instrument may or may not have jaws that can articulate or pivot with respect to the elongate member 14.

Figure 6:
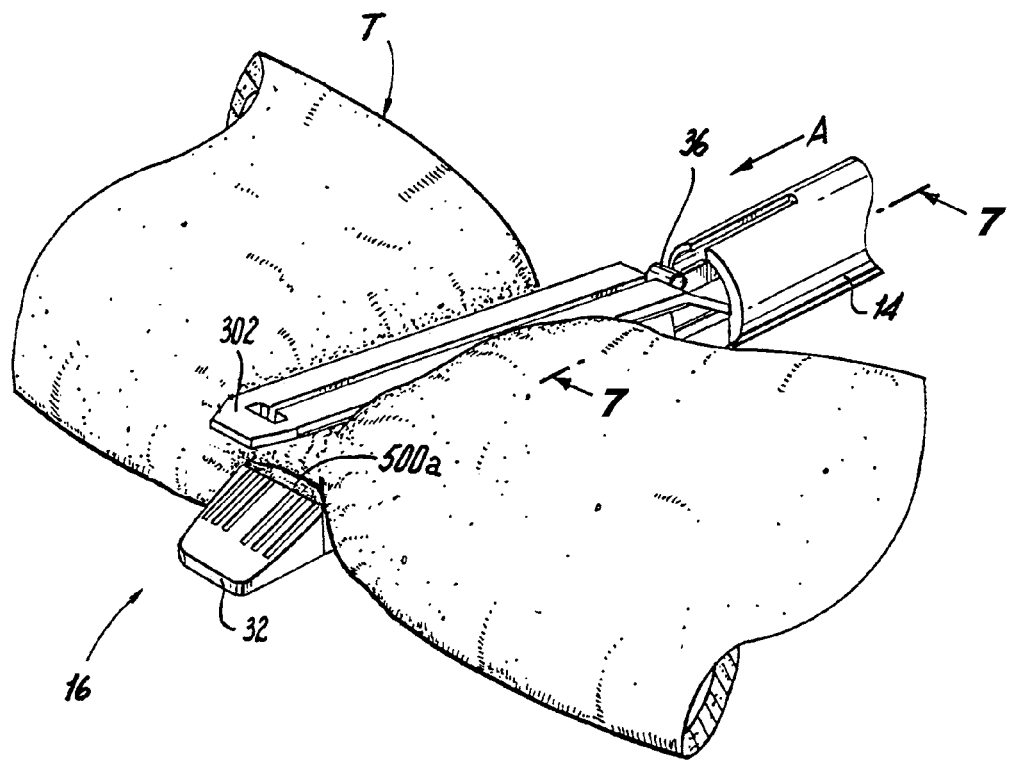
FIG. 6 is a perspective view of a distal end of the surgical stapling apparatus of FIG. 1, shown in use positioned about a tissue section.

A driver 36, as seen in FIGS. 6 and 7A, is provided to move or approximate first jaw or staple cartridge assembly 200 and second jaw or anvil assembly 300 from the open position to the closed position. Driver 36 moves through a longitudinal slot 338 (FIG. 3) formed in the anvil plate 302 of anvil assembly 300. A knife 30 with knife blade 31 is associated with driver 36 to cut tissue captured between staple cartridge assembly 200 and anvil assembly 300 as driver 36 passes through slot 338. The driver desirably engages both the cartridge assembly and the anvil assembly to clamp tissue, and travels through a slot in the staple cartridge that corresponds to slot 338.

Reference may be made to commonly owned U.S. Pat. Nos. 5,915,616, 6,330,965, and 6,241,139, referenced above, for a detailed discussion of the construction and operation of an exemplary surgical stapling apparatus 10.

Staple cartridge assembly 200 and/or anvil assembly 300 may be provided with a surgical buttress 500. Surgical buttress 500 is provided to reinforce and seal the lines of staples applied to tissue by surgical stapling apparatus 10. Surgical buttress 500 may be configured into any shape, size, or dimension suitable to fit any surgical stapling, fastening, or firing apparatus.

Staple cartridge assembly 200 is provided with a cartridge buttress 500a and anvil assembly 300 is provided with an anvil buttress 500b in the manners described in more detail hereinbelow. The buttresses 500a, 500b may be made from any biocompatible natural or synthetic material. The material from which the buttresses 500a, 500b are formed may be bioabsorbable or non-bioabsorbable. It should be understood that any combination of natural, synthetic, bioabsorbable and non-bioabsorbable materials may be used to form the buttress material. The buttresses 500a, 500b may be porous or non-porous, combination of porous and non-porous layers. The non-porous buttresses 500a, 500b may be utilized to retard or prevent tissue ingrowth from surrounding tissues thereby acting as an adhesion barrier and preventing the formation of unwanted scar tissue. For example, the buttress material can include polyglycolic acid, glycolide, trimethylene carbonate, animal derived materials such as porcine or bovine collagen, etc. The buttress material can be formed as a sheet that is molded or extruded, for example; non-woven materials, mesh materials, foams and the like are also contemplated.

Additional exemplary materials for surgical buttresses 500a, 500b for use with the surgical stapling devices disclosed herein are set forth in commonly assigned U.S. Pat. Nos. 5,542,594; 5,908,427; 5,964,774; and 6,045,560, and commonly assigned U.S. Application Publication Nos. 2006/0085034, filed on Apr. 20, 2006; and 2006/0135992, filed on Jun. 22, 2006, the entire contents of each of which is incorporated herein by reference.

As illustrated in the current embodiment and shown in FIGS. 2 and 3, surgical buttress 500 is releasably attached to staple cartridge assembly 200 and/or anvil assembly 300 by strategically positioned adhesive members or tapes 240, 340 that affix surgical buttresses 500a, 500b to the inwardly facing or tissue contacting surfaces 220, 320 of the staple cartridge 32 and/or the anvil plate 302, as discussed in detail below.

Figure 2:
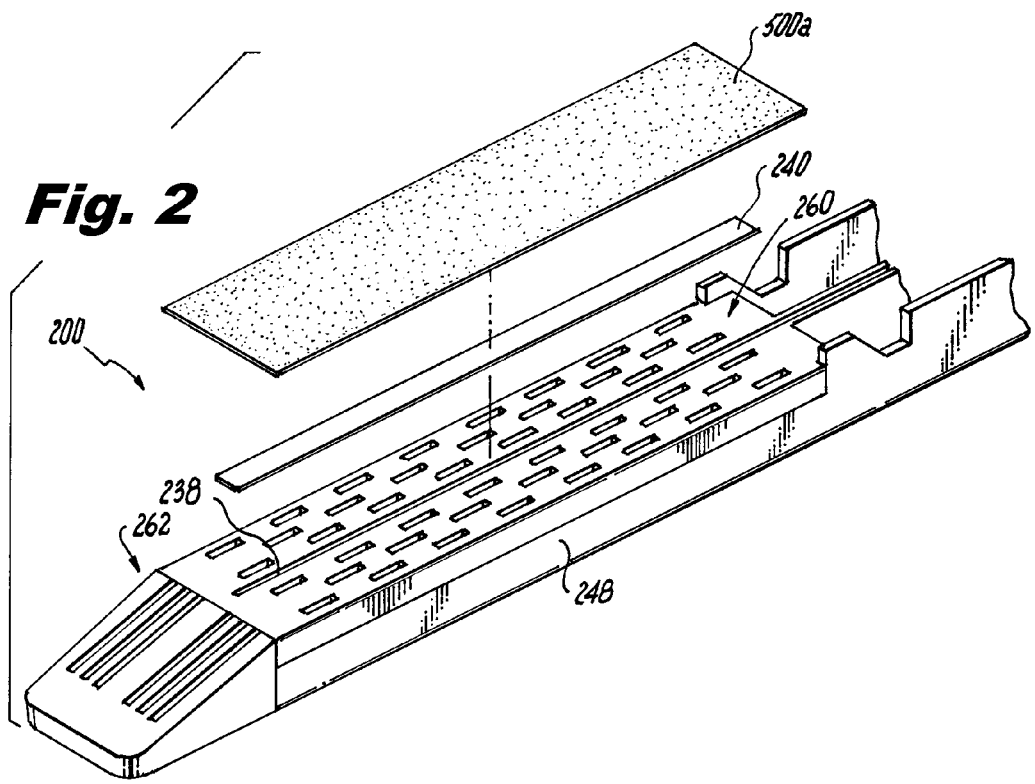
FIG. 2 is a perspective view, with parts separated, of a staple cartridge assembly of the surgical stapling apparatus of FIG. 1, illustrating a surgical buttress associated therewith.

With reference to FIG. 2, cartridge buttress 500a of staple cartridge assembly 200 is operatively secured or adhered to a tissue contacting surface 220 of staple cartridge 32, by an adhesive tape 240 positioned adjacent to and over a central longitudinal slot 238 along the tissue contacting surface 220. Adhesive tape 240 is disposed between the cartridge buttress 500a and the tissue contacting surface 220. Adhesive tape 240 extends longitudinally from a proximal end 260 to a distal end 262 of staple cartridge 32. FIG. 2 illustrates adhesive tape 240 as one single piece, however, adhesive tape 240 may comprise a plurality of small pieces spaced longitudinally along tissue contacting surface 220. The length and width of adhesive tape 240 may vary depending on the staple cartridge 32. Preferably, adhesive tape 240 does not extend over the staple retaining slots 52 of staple cartridge 32. More specifically, adhesive tape 240 is disposed on the tissue contacting surface 220 surrounding the edges 248 of the central longitudinal slot 238 (FIG. 4A) and does not cover the staple retaining slots 52 of staple cartridge 32. By allowing staple retaining slots 52 to remain uncovered by adhesive tape 240, staples 50 may penetrate tissue without any additional obstacles. Cartridge buttress 500a is preferably laser welded onto the adhesive tape 240. Other methods of binding or securing the cartridge buttress 500a to the adhesive tape 240 are contemplated such as ultrasonic welding, solvent bonding, or heat pressing.

For example, in an embodiment, it is contemplated that an applicator (not shown) may be used to deliver (e.g., such as by a spray or aerosol) adhesive material, while in a liquid or fluid state, to tissue contacting surface 220 of staple cartridge 32. The cartridge buttress 500a may then be placed atop the liquid adhesive material. Alternately, the liquid or fluid adhesive material may be allowed to partially cure or dry for a period of time, so as to retain a certain degree of tackiness or adhesive property, after which cartridge buttress 500a may then be placed atop and adhered to the partially cured or dried adhesive material. Alternately still, the liquid or fluid adhesive material may be of a certain composition and allowed to completely cure or dry, wherein the fully cured or dried adhesive material retains a certain degree of tackiness or adhesive property, after which cartridge buttress 500a may then be placed atop and adhered to the fully cured or dried adhesive material. While the foregoing has been directed to the staple cartridge it is understood that similar alternative constructions may be utilized for the anvil plate.

Figure 3:
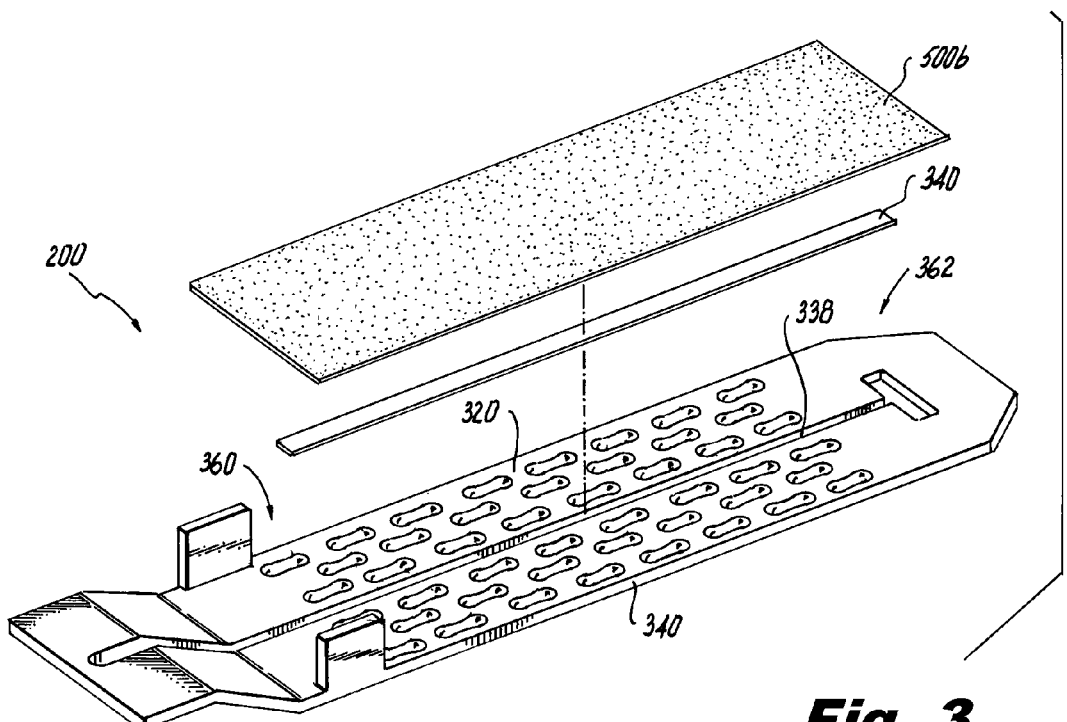
FIG. 3 is a perspective view, with parts separated, of an anvil assembly of the surgical stapling apparatus of FIG. 1, illustrating a surgical buttress associated therewith.

With reference to FIG. 3, and similar to cartridge buttress 500a, anvil buttress 500b is operatively secured or adhered to a tissue contacting surface 320 of anvil plate 302 of anvil assembly 300 by an adhesive tape 340 surrounding the edges 348 of the central longitudinal slot 338 along the tissue contacting surface. Adhesive tape 340 extends from a proximal end 360 and a distal end 362. Preferably, adhesive 340 does not extend over the staple forming pockets 68 of anvil plate 302.

Figure 4A:
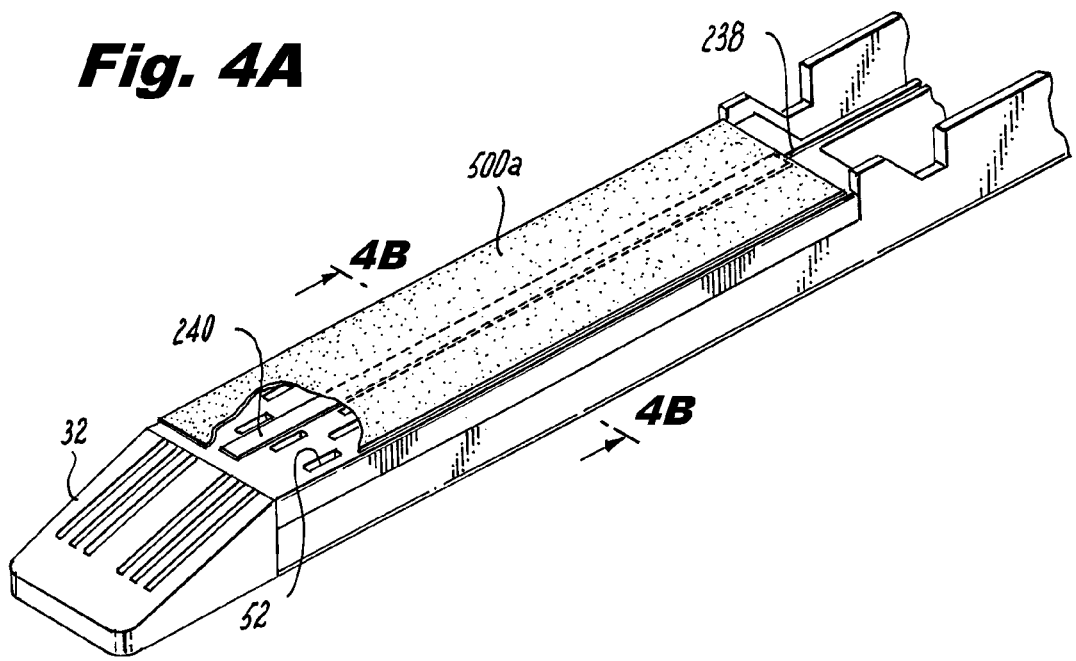
FIG. 4A is a perspective view of the staple cartridge assembly, illustrating the surgical buttress affixed to a staple cartridge.
Figure 4B:
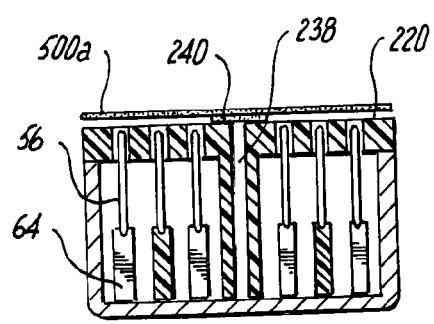
FIG. 4B is a cross-sectional view taken along line 4B-4B of FIG. 4A.
Figure 5:
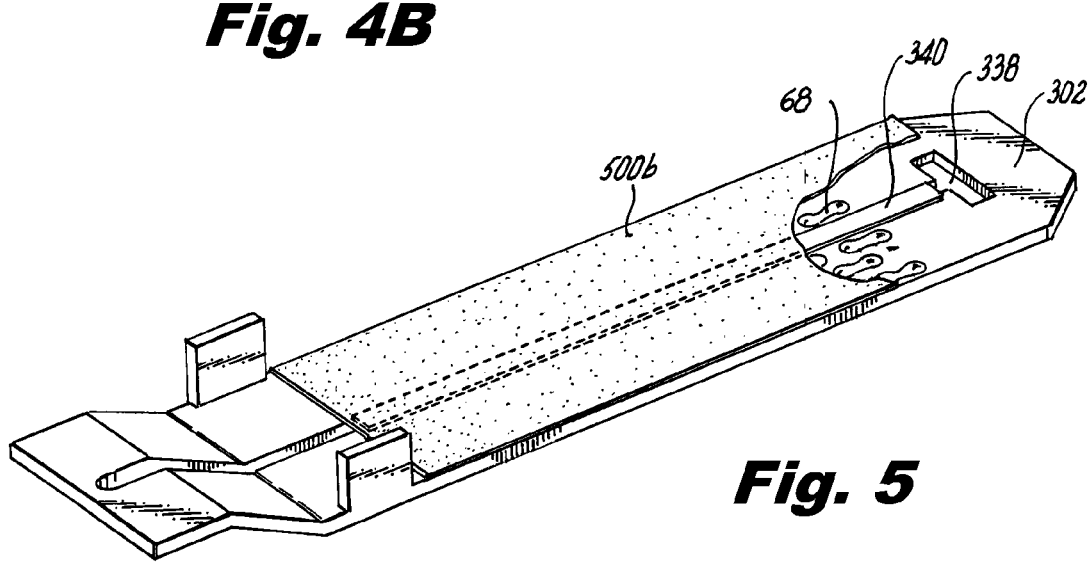
FIG. 5 is a perspective view of the anvil assembly, illustrating the surgical buttress affixed to an anvil plate.

FIGS. 4A and 5 illustrate the buttresses 500a, 500b disposed on the staple cartridge 32 and anvil plate 302, respectively. As shown, adhesive tapes 240, 340 are disposed over the respective central longitudinal slots 238, 338 and between the tissue contacting surfaces 220, 320 and the buttresses 500a, 500b. FIG. 4B shows a cross-sectional view of the cartridge buttress 500a disposed on the staple cartridge 32 showing the adhesive tape 240 disposed between the cartridge buttress 500a and the tissue contacting surface 220. Further adhesive tape 240 is disposed over and surrounding the edges 248 of the central longitudinal slot 238. While FIG. 4B is directed to the staple cartridge it is understood that a similar construction is utilized for the anvil plate. In accordance with the present disclosure, adhesive tapes 240, 340 do not extend over the staple forming recesses 68 of anvil plate 302 or over the staple retaining slots 52 of the staple cartridge 32, respectively.

The adhesive tapes 240, 340 may be of varying widths and thickness depending upon the staple cartridge 32 and anvil plate 302. Preferably, the adhesive tapes 240, 340 are 0.086 inches in width and between 0.002-0.004 inches in thickness. Generally, the central longitudinal slots 238, 338 are 0.050 inches in width. Therefore, the adhesive tapes 240, 340 extend 0.018 inches over each of the edges 248, 348 of the respective central longitudinal slots 238, 338 of each of the staple cartridge 32 and anvil plate 302. However, other shapes and sizes are contemplated, the configuration of the adhesive member or adhesive tape being dependent on the type of stapler.

During assembly adhesive tapes 240, 340 are placed onto each of the tissue contacting surfaces 220, 320 of staple cartridge assembly 200 and anvil assembly 300, respectively. Buttresses 500a, 500b are next placed atop the adhesive tapes 240, 340 and laser welded thereto.

As illustrated in FIG. 6, during use of surgical stapling apparatus 10, the first jaw or staple cartridge assembly 200 and the second jaw or anvil assembly 300, having surgical buttresses 500a, 500b loaded thereon (as described above) are positioned on either side of the surgical site. Tissue contacting surfaces 220, 320 of staple cartridge assembly 200 and anvil assembly 300 are positioned adjacent layers of tissue "T" to be fastened to one another.

Figure 7:
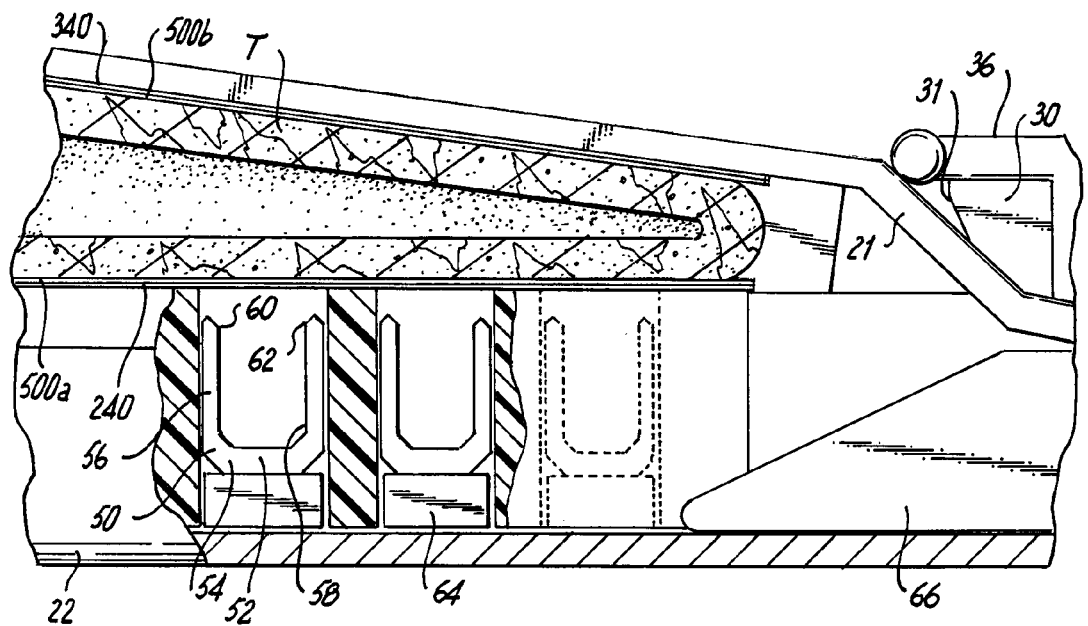
FIG. 7 is a cross-sectional view taken along line 7-7 of FIG. 6.

As shown in FIG. 7, staple cartridge assembly 200 includes surgical staples 50 positioned within individual staple retaining slots 52 of staple cartridge 32. Staples 50 are of a conventional type and include a backspan 54 having a pair of legs 56 and 58 extending from backspan 54. Legs 56 and 58 terminate in tissue penetrating tips 60 and 62, respectively. Pushers 64 are located within staple retaining slots 52 and are positioned between staples 50 and the path of a drive bar 66.

In the illustrated embodiment, surgical stapling apparatus 10 is initially actuated by movement of trigger 33 relative to handle 12 (FIG. 1) causing driver 36 to move in the direction of arrow "A" (FIG. 6), and against sloped edge 21 of anvil plate 302 thereby causing anvil assembly 300 to be moved to the closed position relative to staple cartridge assembly 200. As drive bar 66 advances distally within staple cartridge 32, drive bar 66 urges pushers 64 upwardly against backspan 54 of staples 50 driving legs 56 and 58 of staples 50 through the cartridge buttresses 500a, tissue "T", and anvil buttress 500b, towards staple forming pockets 68 in anvil plate 302 of anvil assembly 300. Tissue penetrating tips 60 and 62 of staple legs 56 and 58 are bent within staple forming pockets 68 in anvil plate 302 with backspan 54 securing surgical buttress 500 against tissue "T". The firing force of the surgical stapling apparatus 10 begins to break the bond between the buttresses 500a, 500b and adhesive tapes 240, 340.

In alternate embodiments, if adhesive tapes 240, 340 are fabricated from bio-absorbable materials, it is contemplated that the firing force of the surgical stapling apparatus 10 begins to break the bond between the buttresses 500a, 500b and respective tissue contacting surfaces of staple cartridge 32 and anvil plate 302.

Opening end effector assembly 16, after firing, releases the bond between the buttresses 500a, 500b and adhesive tapes 240, 340 in order to release the buttresses 500a, 500b from the respective tissue contacting surfaces 220, 320 of the staple cartridge 32 and anvil plate 302. Upon full actuation of surgical stapling apparatus 10, a knife 30 (FIG. 7) associated with surgical stapling apparatus 10 and carried by driver 36 is utilized to cut tissue "T", as well as surgical buttresses 500a, 500b and adhesive tapes 240, 340 between the rows of now formed staples 50. Upon movement of anvil assembly 300 to the open position, spaced apart from staple cartridge assembly 200, buttresses 500a, 500b are pulled away from the adhesive tapes 240, 340, respective tissue contacting surfaces 220, 320 of respective staple cartridge assembly 200 and anvil assembly 300.

Figure 8:
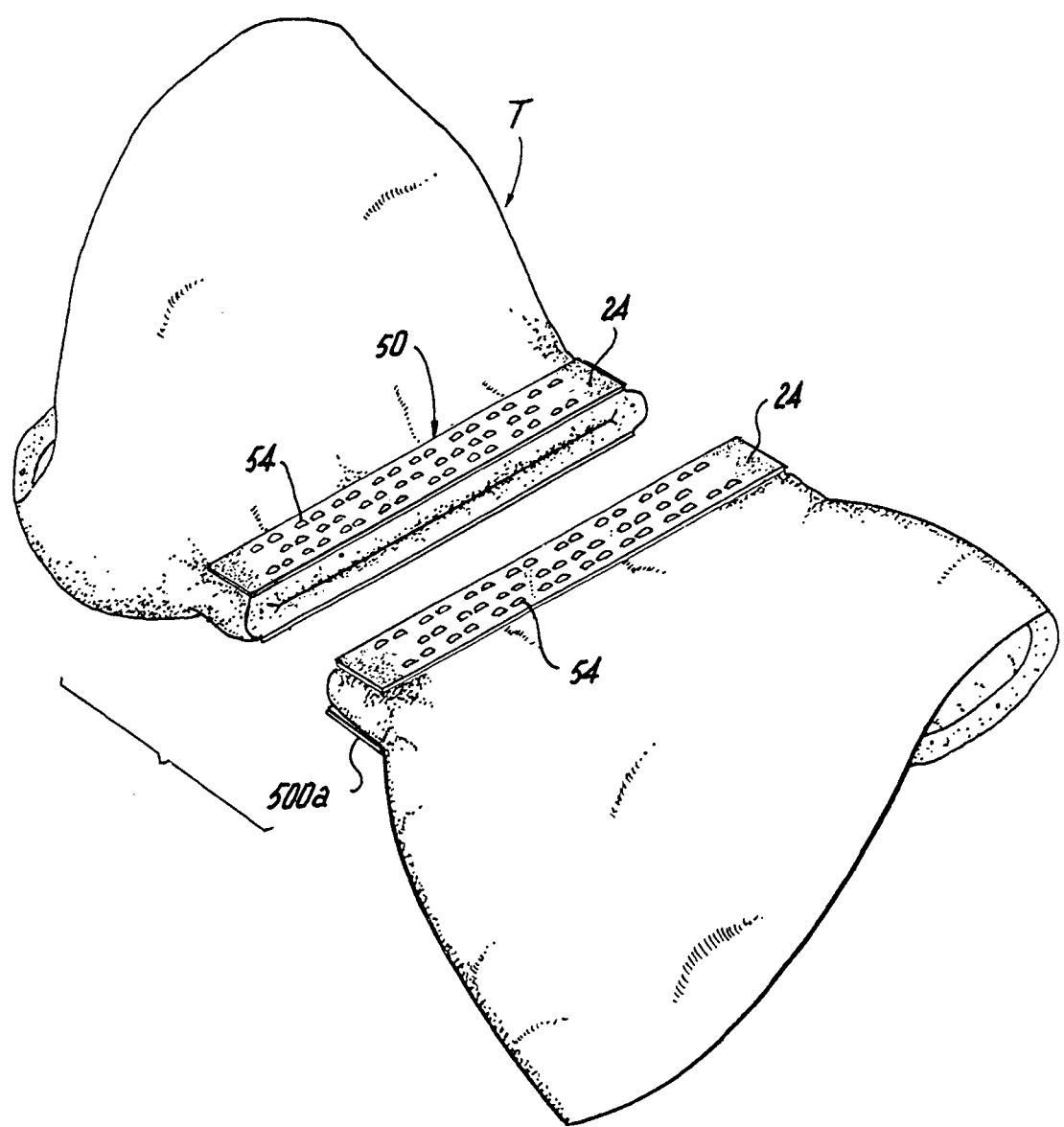
FIG. 8 is a perspective view of the stapled and divided tissue section of FIG. 6.

The resulting tissue "T", divided and stapled closed with staples 50, is illustrated in FIG. 8. Specifically, surgical buttresses 500a, 500b are secured against tissue "T" by legs 56, 58 and backspans 54 of staples 50. Thus, surgical buttresses 500a, 500b are stapled to tissue "T" thereby sealing and reinforcing the staple lines created by staples 50.

Figure 9A:
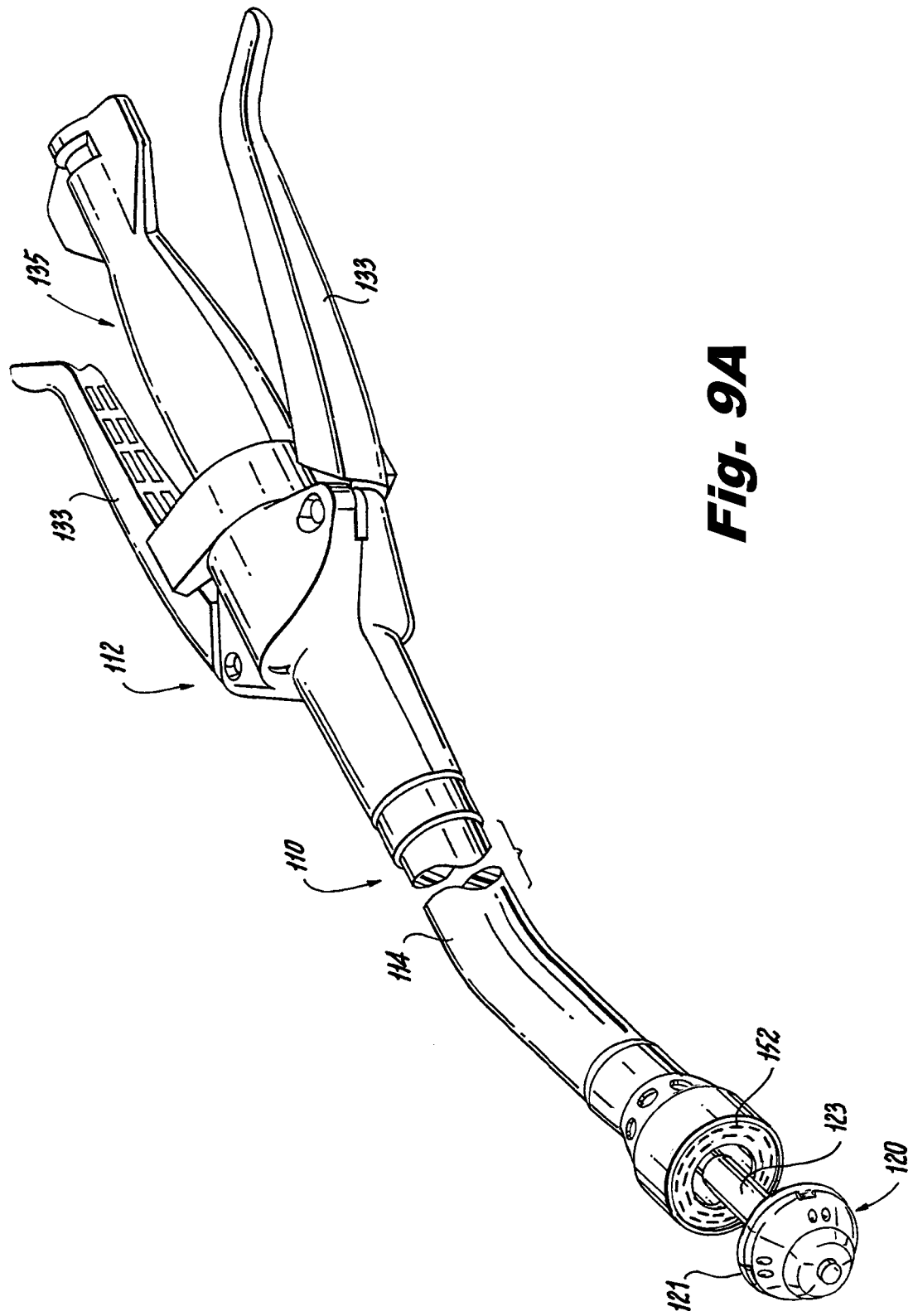
FIG. 9A is a perspective view of an illustrative embodiment of a surgical stapling apparatus in accordance with another embodiment of the present disclosure.
Figure 9B:
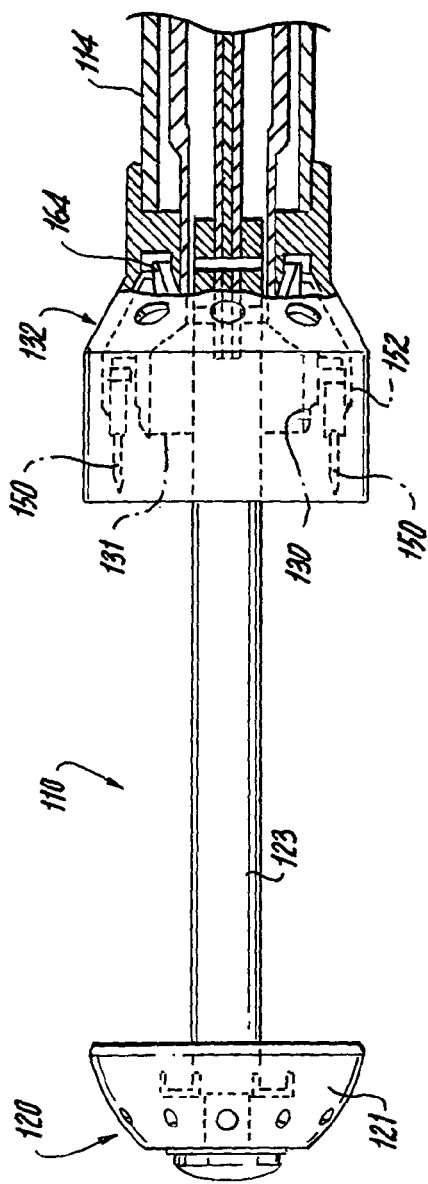
FIG. 9B is a side elevational view, partially broken away, of the surgical stapling apparatus of FIG. 9A.

Referring now to FIGS. 9A and 9B, an annular surgical stapling apparatus 110, for use with surgical buttresses 124 of the present disclosure, is shown. Surgical stapling apparatus 110 includes a handle assembly 112 having at least one pivotable actuating handle member 133, and an advancing member 135. Extending from handle member 112, there is provided a tubular body portion 114 which may be constructed so as to have a curved shape along its length. Body portion 114 terminates in a staple cartridge assembly 122 which includes a pair of annular arrays of staple retaining slots 152 having a staple 150 disposed in each one of staple retaining slots 152. Positioned distally of staple cartridge 122 there is provided an anvil assembly 120 including an anvil member 121 and a shaft 123 operatively associated therewith for removably connecting anvil assembly 120 to a distal end portion of stapling apparatus 110.

Staple cartridge assembly 122 may be fixedly connected to the distal end of tubular body portion 114 or may be configured to concentrically fit within the distal end of tubular body portion 114. Staple cartridge assembly 122 includes a staple pusher 164 including a proximal portion having a generally frusto-conical shape and a distal portion defining two concentric rings of peripherally spaced fingers (not shown), each one of which is received within a respective staple retaining slot 152.

A knife 130, substantially in the form of an open cup with the rim thereof defining a knife blade 131, is disposed within staple cartridge assembly 122 and mounted to a distal surface of a staple pusher 164. The knife 130 is disposed radially inward of the pair of annular arrays of staples 150. Accordingly, in use, as the staple pusher 164 is advanced, the knife 130 is also advanced axially distally.

Figure 10B:
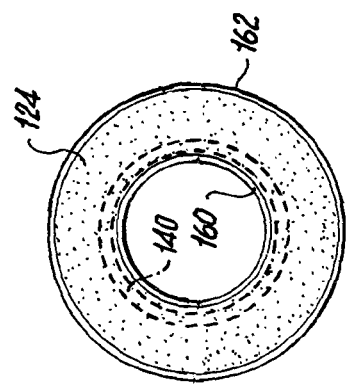
FIG. 10B is a top plan view of the staple cartridge assembly and surgical buttress illustrated in FIG. 10A.
Figure 10A:
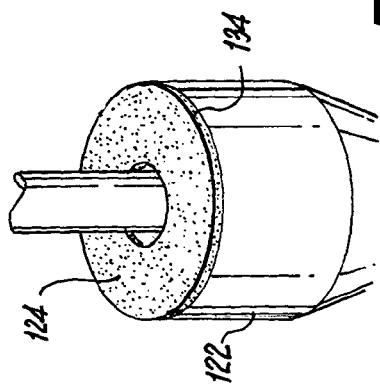
FIG. 10A is a perspective view of an illustrative embodiment of the staple cartridge assembly of the surgical stapling apparatus of FIG. 9A including a surgical buttress in accordance with an embodiment of the present disclosure.

As seen in FIG. 10A, a surgical buttress 124 is releasably attached to the staple cartridge assembly 122 an adhesive tape 140 disposed between the surgical buttress 124 and the tissue contacting surface 134 of the staple cartridge assembly 122. As described herein above, adhesive tape 140 bonds the surgical buttress 124 to the tissue contacting surface 134. Surgical buttress 124 is provided in an annular configuration and includes a central aperture 125 to receive shaft 123 of anvil assembly 120 therethrough.

It is envisioned that the surgical buttress 124 may be additionally or alternatively attached or adhered to tissue contacting surface of anvil plate 121 in a manner similar to the surgical buttress 124 attached to staple cartridge assembly 122.

As shown in FIG. 10B, surgical buttress 124 may be secured or adhered to the staple cartridge 122 along an inner portion 160. It is envisioned that other configurations may be utilized to retain the surgical buttress 124 to the staple cartridge assembly 122, such as placing of adhesive tape 140 along the outer portion 162, or alternating a plurality of pieces of adhesive tapes 140 between the inner portion 160 and outer portion 162, or among other arrangements within the purview of those skilled in the art.

Surgical stapling apparatus 110 and detachable anvil assembly 120 are used in an anastomosis procedure to effect joining of intestinal sections 50 and 52. The anastomosis procedure is typically performed using minimally invasive surgical techniques including laparoscopic means and instrumentation. At the point in the procedure shown in FIG. 11, a diseased intestinal section has been previously removed, anvil assembly 120 (optionally including a surgical buttress 124 thereon) has been applied to the operative site either through a surgical incision or transanally and positioned within intestinal section 52, and tubular body portion 114 of surgical stapling apparatus 110 (optionally including a surgical buttress 124 thereon) has been inserted transanally into intestinal section 50. Intestinal sections 50 and 52 are also shown temporarily secured about their respective components (e.g., shaft 123 of anvil assembly 120, and the distal end of tubular body portion 114) by conventional means such as a purse string suture "P", as illustrated in FIG. 12.

Thereafter, the clinician maneuvers anvil assembly 120 until the proximal end of shaft 123 is inserted into the distal end of tubular body portion 114 of surgical stapling apparatus 110, wherein the mounting structure (not shown) within the distal end of tubular body portion 114 engages shaft 123 to effect the mounting. Anvil assembly 120 and tubular body portion 114 are then approximated to approximate intestinal sections 50, 52. Surgical stapling apparatus 110 is then fired. A knife (not shown) cuts the portion of tissue and surgical buttress 124 disposed radially inward of the knife, to complete the anastomosis. The force of the opening of anvil assembly 120 and staple cartridge assembly 122, with surgical buttress 124 stapled to intestinal sections 50 and 52, causes surgical buttress 124 to release at the attachment pads 140 thereby releasing the surgical buttress 124 from the tissue contacting surface 134.

Persons skilled in the art will understand that the devices and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another exemplary embodiment without departing from the scope of the present disclosure, and that such modifications and variations are also intended to be included within the scope of the present disclosure. Accordingly, the subject matter of the present disclosure is not to be limited by what has been particularly shown and described, except as indicated by the appended claims.

What is claimed is:

1. An end effector for use with a surgical apparatus, the end effector comprising:
    a staple cartridge having a tissue contacting surface defining a central longitudinal slot and staple retaining slots;
    an anvil plate having a tissue contacting surface defining a central longitudinal slot and staple forming pockets;
    a first surgical buttress releasably disposed on the tissue contacting surface of the staple cartridge; and
    a first adhesive tape disposed over the central longitudinal slot of the staple cartridge and not covering the staple retaining slots of the staple cartridge, the first adhesive tape secured to the tissue contacting surface of the staple cartridge at locations surrounding edges of the central longitudinal slot to retain the first surgical buttress atop the tissue contacting surface of the staple cartridge.

2. The end effector of claim 1, wherein the first surgical buttress is laser welded to the first adhesive tape.

3. The end effector of claim 1, wherein the first adhesive tape extends longitudinally between a proximal end and a distal end of the tissue contacting surface of the staple cartridge.

4. A staple cartridge for use with a surgical stapling apparatus, the staple cartridge comprising:
    a cartridge body including a tissue contacting surface defining a plurality of staple retaining slots and having a central longitudinal slot;
    a staple disposed within each staple retaining slot of the cartridge body;
    a surgical buttress releasably disposed on the tissue contacting surface of the cartridge body; and
    an adhesive tape disposed over the central longitudinal slot of the cartridge body and not covering the plurality of staple retaining slots of the cartridge body, the adhesive tape secured to the tissue contacting surface of the cartridge body at locations surrounding edges of the central longitudinal slot to retain the surgical buttress atop the tissue contacting surface of the cartridge body.

5. The staple cartridge of claim 4, wherein the surgical buttress is laser welded to the adhesive tape.

6. The staple cartridge of claim 4, wherein the adhesive tape extends longitudinally between a proximal end and a distal end of the tissue contacting surface of the cartridge body.

7. A surgical stapling apparatus, comprising:
    a housing;
    an end effector secured to the housing, the end effector including a staple cartridge assembly having a tissue contacting surface and staple retaining slots, and an anvil assembly having a tissue contacting surface, each of the staple cartridge assembly and the anvil assembly having a central longitudinal slot;
    a first surgical buttress releasably disposed on the tissue contacting surface of the staple cartridge assembly; and
    a first adhesive tape disposed over the central longitudinal slot of the staple cartridge assembly and not covering the staple retaining slots of the cartridge body, the first adhesive tape secured to the tissue contacting surface of the staple cartridge assembly at locations surrounding edges of the central longitudinal slot to retain the first surgical buttress atop the tissue contacting surface of the staple cartridge assembly.

8. The surgical stapling apparatus of claim 7, wherein the first surgical buttress is laser welded to the first adhesive tape.

9. The surgical stapling apparatus of claim 7, wherein the first adhesive tape extends longitudinally between a proximal end and a distal end of the tissue contacting surface of the staple cartridge assembly.

10. The end effector of claim 1, further comprising:
    a second surgical buttress releasably disposed on the tissue contacting surface of the anvil plate; and
    a second adhesive tape disposed over the central longitudinal slot of the anvil plate and not covering the staple forming pockets, the second adhesive tape secured to the tissue contacting surface of the anvil plate at locations surrounding edges of the central longitudinal slot to retain the second surgical buttress atop the tissue contacting surface of the anvil plate.

11. The end effector of claim 10, wherein the second surgical buttress is laser welded to the second adhesive tape.

12. The end effector of claim 10, wherein the second adhesive tape extends longitudinally between a proximal end and a distal end of the tissue contacting surface of the anvil plate.

13. The surgical stapling apparatus of claim 7, further comprising:
   a second surgical buttress releasably disposed on the tissue contacting surface of the anvil assembly; and
   a second adhesive tape disposed over the central longitudinal slot of the anvil assembly and not covering staple forming pockets defined in the tissue contacting surface of the anvil assembly, the second adhesive tape secured to the tissue contacting surface of the anvil assembly at locations surrounding edges of the central longitudinal slot to retain the second surgical buttress atop the tissue contacting surface of the anvil assembly.

14. The surgical stapling apparatus of claim 13, wherein the second surgical buttress is laser welded to the second adhesive tape.

15. The surgical stapling apparatus of claim 13, wherein the second adhesive tape extends longitudinally between a proximal end and a distal end of the tissue contacting surface of the anvil assembly.

\* \* \* \* \*